United States Patent
Perkins

(10) Patent No.: US 7,329,261 B2
(45) Date of Patent: Feb. 12, 2008

(54) NO PORT PHACOEMULSIFICATION NEEDLE SLEEVE

(75) Inventor: James T. Perkins, St. Charles, MO (US)

(73) Assignee: Bausch & Lomb Incorporated, Rochester, NY (US)

( * ) Notice: Subject to any disclaimer, the term of this patent is extended or adjusted under 35 U.S.C. 154(b) by 67 days.

(21) Appl. No.: 11/017,114

(22) Filed: Dec. 20, 2004

(65) Prior Publication Data

US 2006/0135976 A1 Jun. 22, 2006

(51) Int. Cl.
*A61F 9/00* (2006.01)
(52) U.S. Cl. .......................... 606/107; 604/22
(58) Field of Classification Search ............ 604/22, 604/158, 164.01, 264, 272, 523; 606/107, 606/167–169
See application file for complete search history.

(56) References Cited

U.S. PATENT DOCUMENTS

| 4,493,694 | A | * | 1/1985 | Wuchinich | 604/22 |
| 5,464,389 | A | | 11/1995 | Stahl | |
| 5,746,713 | A | * | 5/1998 | Hood et al. | 604/22 |
| 5,989,209 | A | | 11/1999 | Barrett | |
| 6,299,591 | B1 | * | 10/2001 | Banko | 604/22 |
| 6,340,355 | B1 | | 1/2002 | Barrett | |
| 6,605,054 | B2 | * | 8/2003 | Rockley | 604/22 |
| 7,018,389 | B2 | * | 3/2006 | Camerlengo | 606/166 |
| 2001/0034504 | A1 | | 10/2001 | Zaleski | |
| 2002/0072754 | A1 | * | 6/2002 | Camerlengo | 606/107 |

FOREIGN PATENT DOCUMENTS

EP    1464310 A    10/2004

OTHER PUBLICATIONS

International Search Report (PCT/ISA/210) and Written Opinion (PCT/ISA/237) mailed May 30, 2006.

* cited by examiner

*Primary Examiner*—LoAn H Thanh

(57) ABSTRACT

A phacoemulsification needle sleeve 10 includes an elongated, resilient tubular body portion 18 having a distal end 20. An enlarged section 22 is formed on a proximal end of the body portion 18 for surrounding a hub of a needle 12. The distal end 20 is formed to abut a proximal end 24 of a flared end 14 of the needle 12. An outer diameter of the body portion 18 is essentially equal to an outer diameter of the flared end 14 so that the sleeve 10 is easily inserted through an incision 54 in a patient's eye.

1 Claim, 3 Drawing Sheets

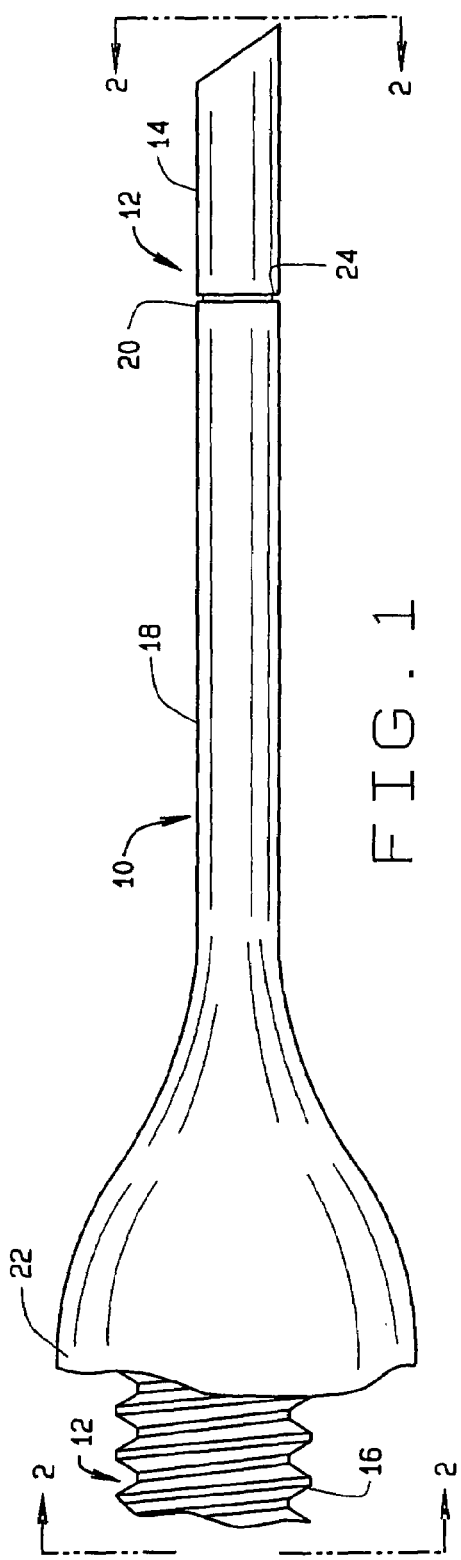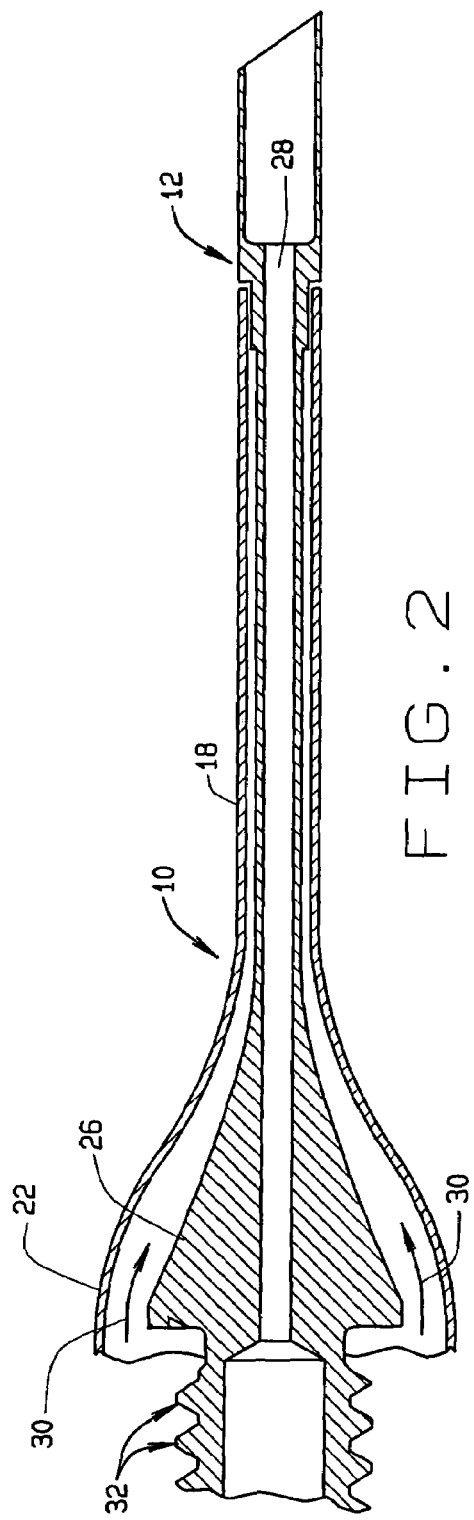

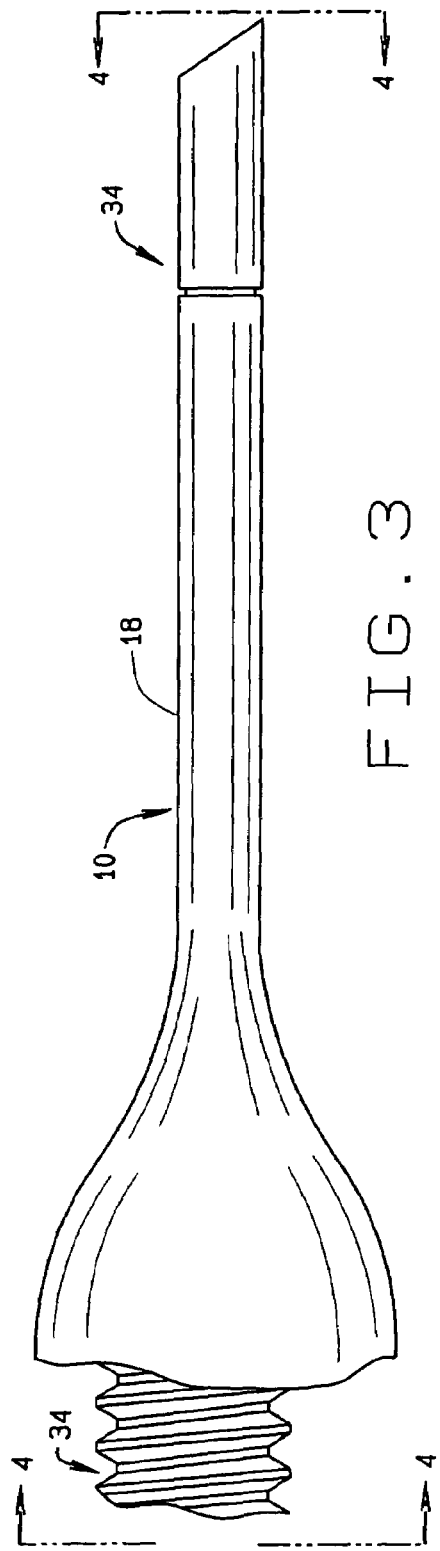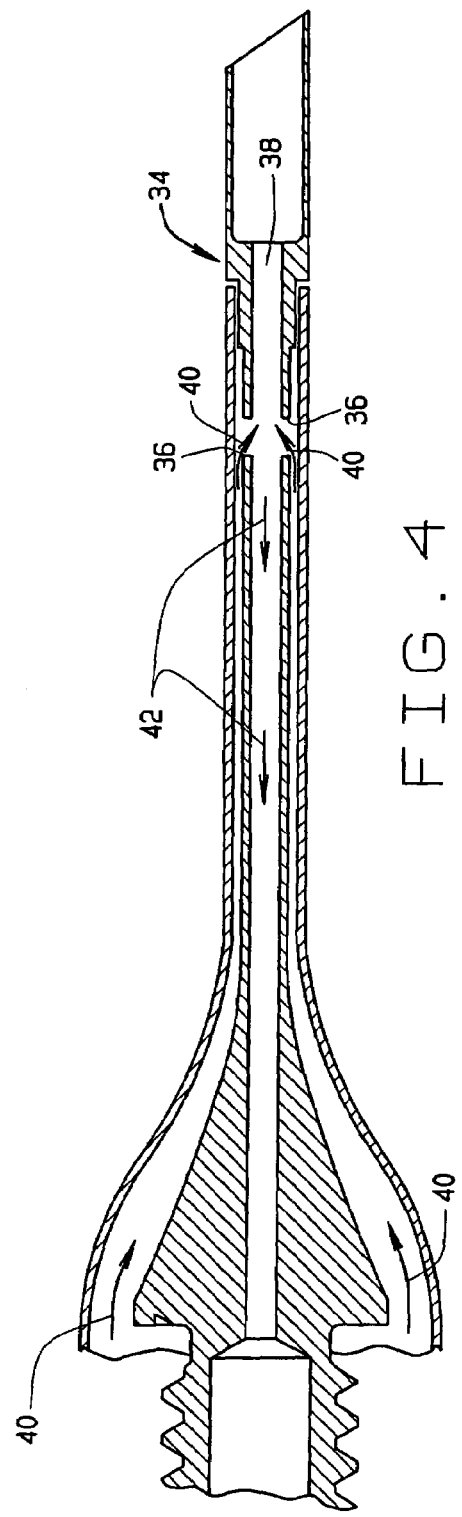

NO PORT PHACOEMULSIFICATION NEEDLE SLEEVE

BACKGROUND OF THE INVENTION

1. Field of the Invention

The present invention is related to phacoemulsification needles used in ophthalmic surgery and more specifically, to sleeves which surround the phacoemulsification needle during surgery.

2. Description of Related Art

It is well known to remove cataracts from a patient's eyes and replace the removed cataract affected lens with an artificial intraocular lens. It is common and accepted practice to remove the cataract affected lens via phacoemulsification.

Phacoemulsification enables the lens to be removed from the eye through a very small incision, typically on the order of 3 mm. Phacoemulsification involves using high frequency ultrasound energy transmitted through a handpiece into a phacoemulsification needle to fragment the affected lens. Once the lens is fragmented or emulsified, the lens material is aspirated along with irrigation fluid through a lumen of the phacoemulsification needle, and through the handpiece and into a collection reservoir of a surgical system.

During aspiration of the lens material it is typical to simultaneously insert a flow of irrigation fluid into the eye. This flow is provided to prevent the eye from collapsing during aspiration. It is also typical that a phacoemulsification needle provides what is commonly referred to as coaxial irrigation. This coaxial irrigation provides the flow of irrigation fluid into the eye via a resilient sleeve surrounding the needle. The irrigation sleeve typically includes irrigation ports at the distal end of the sleeve so that fluid flows from the handpiece in between the sleeve and the outside of the needle. While phacoemulsification and coaxial irrigation has proven to be very successful and safe, there is a strong desire to reduce the incision size even further from the current average incision of 3 mm. One procedure being adopted to accomplish this is a technique known as bi-manual cataract extraction. In bi-manual extraction, there are typically at least two very small incisions made on the order of 1.4 mm in length. In order to accommodate such a small size, the irrigation portion with a separate irrigation cannula is inserted through one incision and a phaco needle with only aspiration and typically no sleeve is inserted through the other incision.

In bi-manual surgery, without the insulative and sealing effects of an outer sleeve around the aspiration needle, there are concerns regarding excessive heating of the corneal tissue due to the vibration of the needle and also fluid leakage around the needle at the incision site.

Therefore, it would advantageous and desirable to have a phacoemulsification needle that provides the insulative and sealing properties of the prior art coaxial phaco needle with a sleeve, without requiring a larger incision size to accommodate the sleeve.

BRIEF DESCRIPTION OF DRAWINGS

FIG. 1 is a side elevation view of a phacoemulsification needle sleeve inserted onto a phaco needle in accordance with the present invention;

FIG. 2 is a cut-away side elevation view of FIG. 1 taken along lines 2-2;

FIG. 3 is a side elevation view of an alternate embodiment of a phacoemulsification needle and sleeve combination in accordance with the present invention;

FIG. 4 is a cut-away side elevation view of FIG. 3 taken along line 4-4;

DETAILED DESCRIPTION OF THE PREFERRED EMBODIMENT

Figure 5:
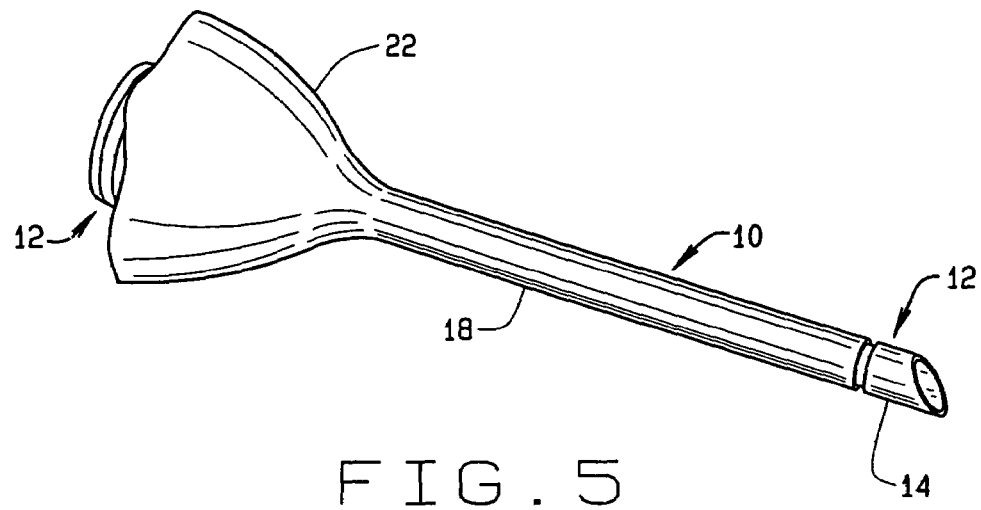
FIG. 5 is a partial perspective view of a needle and sleeve combination in accordance with the present invention.

FIG. 1 shows a phacoemulsification needle sleeve 10, in accordance with the present invention. Sleeve 10 is attached to a phacoemulsification needle 12 having a distal end 14 and a proximal end 16. Proximal end 16 is typically attached to a conventional phacoemulsification handpiece, which may or may not include a port for delivering irrigation fluid between the phacoemulsification needle sleeve 10 and needle 12.

Sleeve 10 includes an elongated, resilient essentially tubular body portion 18 having a distal end 20 and a proximal end 22 for surrounding a portion of a shaft of phacoemulsification needle 12. Proximal end 22 includes an enlarged section, as shown, formed on the proximal end of the body portion 18 for surrounding a hub (shown below in FIG. 2) of the needle 12. The distal end 20 is formed to abut a proximal end 24 of a flared end 14 of the needle 12. In this way, an outer diameter of the body portion 18 is essentially equal to an outer diameter of the flared end 14, as can be seen in FIG. 1. This allows the sleeve 10 surrounding needle 12 to be easily inserted through an incision in a patient's eye during surgery of less than 2 mm in length.

The sleeve 10 is typically formed of silicone or other pliable, resilient materials suitable for use in surgery. In this way, sleeve 10 performs both an insulative and sealing function for use during cataract surgery.

FIG. 2 shows a cut-away view of FIG. 1 taken along line 2-2. As can be seen, enlarged section of the proximal end 22 surrounds a phaco needle hub 26 of needle 12. During surgery, emulsified cataract tissue and irrigation fluid is aspirated through lumen 28 into a phaco handpiece, not shown, and eventually into a collection reservoir of a pumping system of an ophthalmic surgical system, such as that available from Bausch & Lomb Incorporated. Irrigation fluid may be introduced to surround needle 12 and be contained by sleeve 18 and will initially flow in the direction of arrows 30. The introduction of such irrigation fluid provides for more insulative and sealing effects for sleeve 10 than without such fluid being introduced between needle 12 and the sleeve 10. Threads 32 typically engage a well-known phacoemulsification handpiece.

FIG. 3 shows a sleeve 10 surrounding a needle 34 to form an alternate embodiment, in accordance with the present invention. The needle 34 and sleeve 10 are essentially identical to that described above with respect to FIGS. 1 and 2, except that as seen in FIG. 4, needle 34 includes at least one hole 36 and preferably two, as shown. Holes 36 allow irrigation fluid to flow into an inner aspiration lumen 38 of the needle 34. Irrigation fluid flows in the direction of arrows 40 from a phacoemulsification handpiece in a well-known standard manner, and continually flows into the aspiration lumen 38, wherein the irrigation fluid is aspirated away from the surgical site and into a collection reservoir, not shown, in the direction of arrows 42. A needle 34 with such holes 36 allows for the continuing flow of irrigation fluid around needle 34 and thus provides even greater cooling and insulative effects compared to the needle of FIGS. 1 and 2.

FIG. 5 is a partial perspective view of the sleeve needle combination of FIG. 1, and shows sleeve 10 surrounding needle 12. It is important that the outer diameter of the tubular portion 18 be essentially equal to the outer diameter of flared end 14 of needle 12 so that the sleeve and needle combination are easily inserted into an eye during surgery. If the sleeve outer diameter of tubular body portion 18 is too much greater than the outer diameter of flared end 14, there is a risk and likelihood that the sleeve 10 will not pass into the eye and remain surrounding the needle 12 as desired; but rather will become bunched-up around the outside of the incision in the cornea.

Figure 6:
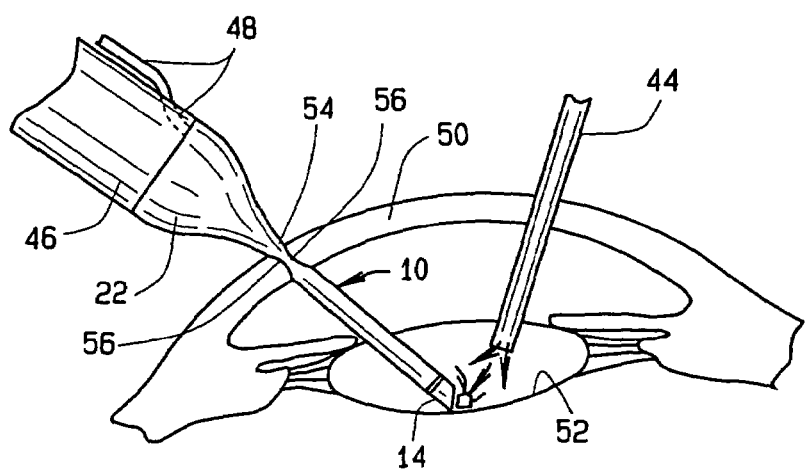
FIG. 6 is a cut-away elevation view of a phacoemulsification needle in accordance with the present invention being used during surgery.

It is also important that sleeve 18 be devoid of any irrigation ports, as shown. Irrigation ports are commonly found in sleeves for phacoemulsification needles having coaxial irrigation, and such ports are typically found at the distal end of the sleeve, in order to introduce irrigation fluid into the eye. However, during a bi-manual procedure, as shown in FIG. 6, irrigation fluid is typically introduced into the eye to keep the eye from collapsing through a needle, such as needle 44 shown. The sleeve 10 and needle 12 are typically connected to a phacoemulsification handpiece 46 that may or may not have an irrigation source 48 and is inserted through a cornea 50 and into a capsular bag 52, as shown. Incision 54 in cornea 50 will typically compress sleeve 10 about needle 12, as shown at lines 56. Lines 56 are exaggeratingly curved in order to illustrate the effect of the incision 54 on the sleeve 10. In this way, sleeve 10 provides insulative and sealing properties to prevent leakage of fluid around the incision site during surgery.

Thus has been described an inventive phacoemulsification needle sleeve, in accordance with the present invention. Other variations and alternate embodiments will occur to those skilled in the art without departing from the scope of the present invention.

I claim:

1. A phacoemulsification needle and sleeve assembly comprising:
   an elongated needle having a hub for engaging a handpiece, a shaft connected to the hub, and a flared end connected to the shaft;
   an elongated sleeve having a resilient essentially tubular body portion having a distal end and a proximal end for surrounding a portion of the shaft of the needle;
   wherein the sleeve further includes an enlarged section formed on the proximal end of the body portion for surrounding a hub of the needle; and
   wherein the distal end of the sleeve is formed to abut a proximal end of the needle flared end, such that an outer diameter of the sleeve body portion is essentially equal to an outer diameter of the flared end so that the sleeve is easily inserted through an incision in a patient's eye.

* * * * *